United States Patent [19]

Kufudaki

[11] Patent Number: 5,672,590
[45] Date of Patent: Sep. 30, 1997

[54] PHARMACEUTICAL COMPOSITION FOR IMMUNOMODULATING AND ADJUVANT TREATMENT

[75] Inventor: Olga Kufudaki, Prague, Czech Rep.

[73] Assignee: Aliatros Medical, a.s., Prague, Czech Rep.

[21] Appl. No.: 564,328

[22] PCT Filed: Jul. 12, 1994

[86] PCT No.: PCT/CZ94/00015

§ 371 Date: Apr. 10, 1996

§ 102(e) Date: Apr. 10, 1996

[87] PCT Pub. No.: WO95/02398

PCT Pub. Date: Jan. 26, 1995

[30] Foreign Application Priority Data

Jul. 12, 1993 [CS] Czechoslovakia .................. 1385-93

[51] Int. Cl.$^6$ .................. A61K 31/715; A61K 31/51; A61K 31/44; A61K 31/34; A61K 31/195

[52] U.S. Cl. .................. 514/53; 514/276; 514/356; 514/474; 514/561

[58] Field of Search .................. 514/23, 276, 356, 514/474, 561

[56] References Cited

U.S. PATENT DOCUMENTS 4,514,387 4/1985 Wissler .................. 424/85

*Primary Examiner*—Raymond Henley, III
*Attorney, Agent, or Firm*—Bruce F. Jacobs; Diderico Van Eyl

[57] ABSTRACT

Pharmaceutical composition for immunomodulating and adjuvant therapy containing a metabolic stressor, 2-deoxy-D-ribose and further active components, i.e. ribose, DL-alanine, nicotonic acid, L-ascorbic acid, thiamin and glutamic acid amide is intended for immunomodulating and adjuvant therapy and for prevention of weakening of the immunity system.

21 Claims, 3 Drawing Sheets

CONTROLS: *
SD OF THE CONTROL GROUP: +
TEST GROUPS: ■
SD OF THE TEST GROUP: +

PHARMACEUTICAL COMPOSITION FOR IMMUNOMODULATING AND ADJUVANT TREATMENT

This application is A 371 of PCT/C294/00015 filed Jul. 12, 1994.

FIELD OF INVENTION

The invention concerns a pharmaceutical preparation for immunomodulating and adjuvant treatment and for prevention of weakening of the immunity system.

BACKGROUND OF THE INVENTION

Immunomodulating compositions used at present time for treatment of various immunodeficiencies, autoimmunological and malignant diseases may according to their composition and origin be divided into several groups. An important group of these compositions is formed e.g. by the thymus hormones produced by extraction of animal tissues and distributed under the designation Thymus V-fraction (Hoffmann LaRoche), Thymodulin and Leucotropina (Ellem), Tymunox (Cilag) or TFX (Polfa). A further group of lmmunomodulating compounds to which much attention is paid especially in the field of basic medical research are cytokins, which which are the main compounds controlling the immunity response at the cell level. The technology of gene engineering facilitates the preparation of recombinant proteins which are active components of immunomodulating compositions, e.g. Roferon (interferon alpha2), (Hoffmann LaRoche), or hematopoetic growth factor G-CSF (Hoffmann LaRoche), distributed under he designation Neupogen. The already classic therapy by the use of interleukin-2 was discussed at the congress IMMUNOTHERAPY OF INFECTIONS (Berlin, May 4 to 7, 1993) especially from the wievpoint of failing in a part of the patients. Dialyzates of leucocytes are also very popular immunomodulating agents. In the Czech Republic they are known as Transfer factor (Sevac). To the oldest and still most often used agents belong compounds on the basis of the adjuvant activity of selected antigens derived from the components of bacterial membranes, e.g. Stays (Sevac), Olimostimulin (Medical Faculty of the Palacky University, Olomouc). East medicine, especially in China, pays on the basis of the old tradition very big attention to immunostimulation compounds of plant origin and to the mechanism of their activity on the level of present europian research (Immunotherapy of Infections. Berlin. May 4 to 7, 1993).

A composition known from the Greek Patent Specification No. 72 440 (dr. T. H. Alivizatos), containing a mixture of D-ribose, DL-alanine, nicotinic acid and ascorbic acid may also be considered as a composition having a pronounced immunomodulating activity as this composition is able to rebuild the metabolic equilibrium and to strengthen the immnunity of the organism.

According to the modem conception of immunomodulating therapy targeted actions into the immunity of the organism are performed and it is necessary to define the area of the action and the character of the action of any pharmaceutical preparation. Such a definition is in case of most still used immunomodulating compounds very complicated and difficult. The reason of all these difficulties reside on one side in gaining some of the immunomodulating compounds from biological sources (and it is difficult to define all their possible biological activities, therefore) on the other side all these compounds have a number of biological activities that make the localization of their action in the regulating spheres of the immunity system impossible. Therapy based on the application of individual cytokines is according to present experience complicated by a number of risks which ape the result of involving of autoregulation mechanisms of the recipient of cytokins and successively the efficiency of the immunity system becomes lowered. It is also known that the activation of the immunity system by an exogenous cytokine is not of full value as further natural components are missing. For this reason it would be very desirable to prepare an immunomodulation preparation which would activate the system on a "physiological level", that means under involving all natural regulating and controlling spheres.

DESCRIPTION OF THE INVENTION

The object of the invention resides in a pharmaceutical composition for immunomodulating and adjuvant therapy which contains a metabolic stressor. The invention broadens the knowledge according to the above mentioned Greek Patent Specification according to knew information concerning the regulation of the immunity response and possible affecting of this response by metabolic stressors. A metabolic stressor is a natural non-toxic compound in this case a deoxyderivative of D-monosaccharides which is able to influence the production of cytokines, that means of the real regulators tots of the immunity response on cell level.

The object of the invention is a pharmaceutical composition for immunomodulation and adjuvan therapy containing D-ribose 10–35 g 2-deoxy-D-ribose (the metabolic stressor) 10–35 g DL-alpha-alanine 2–12 g nicotinic acid 2–10 g L-ascorbic acid 7–20 g thiamine 0.2–2 g glutamic acid amide 0.01–15 g the components are dissolved in 1,000 of physiological saline.

The presence of deoxy-derivatives of D-monosaccharides enables a targeted action on the immunity system and the use of the pharmaceutical preparation for treatment of a broader scope of immunity defects and of diseases based on the immunity system, especially of autoimmunity diseases and of tumorous ilnesses in comparison with the abovementioned Greek Patent Specification.

EXAMPLE OF INVENTION

Example 1

Figure 1:
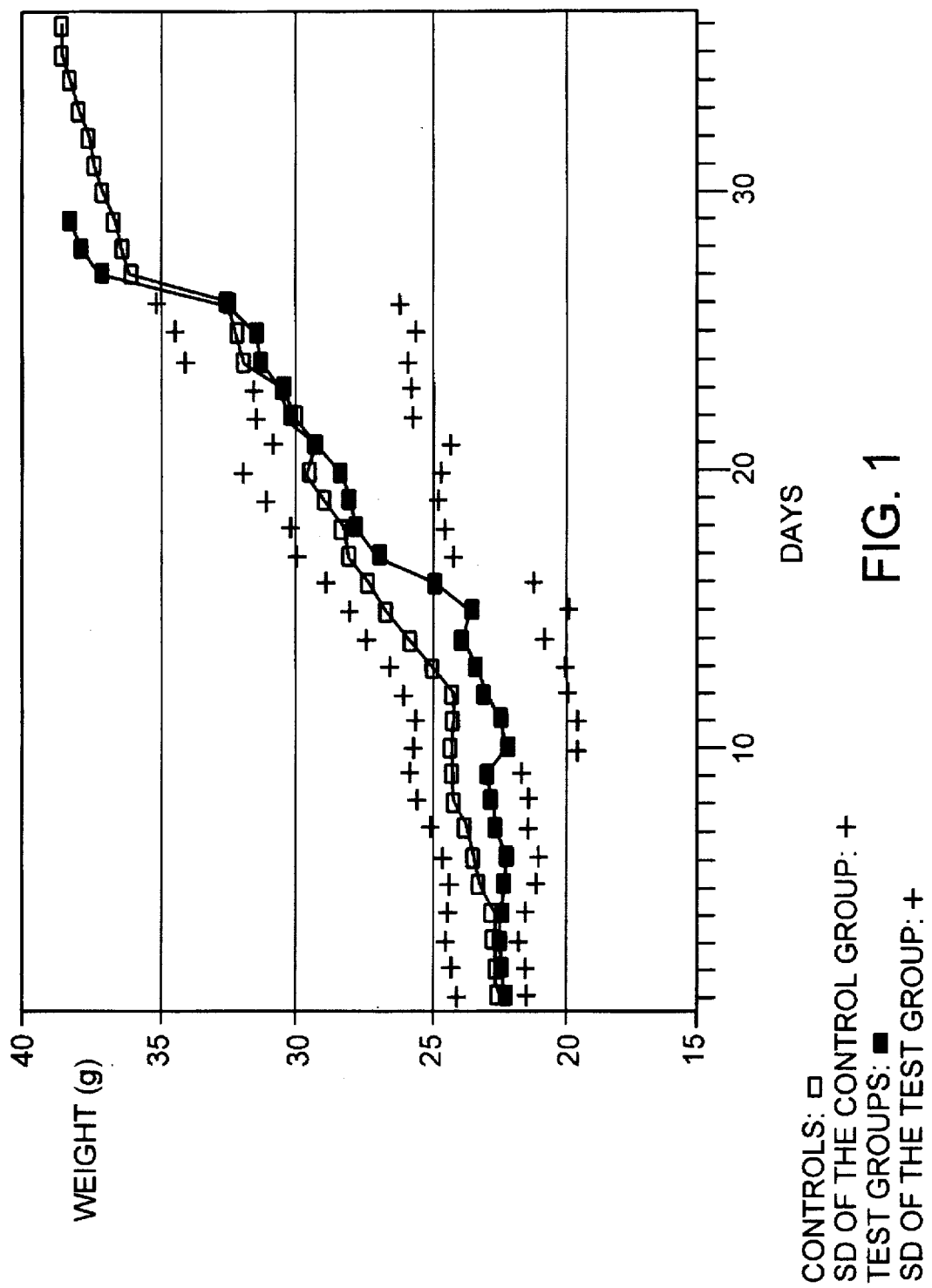
FIG. 1 shows the effect of a composition according to the present invention on the weight of C57B16 mice as compared to a control group.
Figure 2:
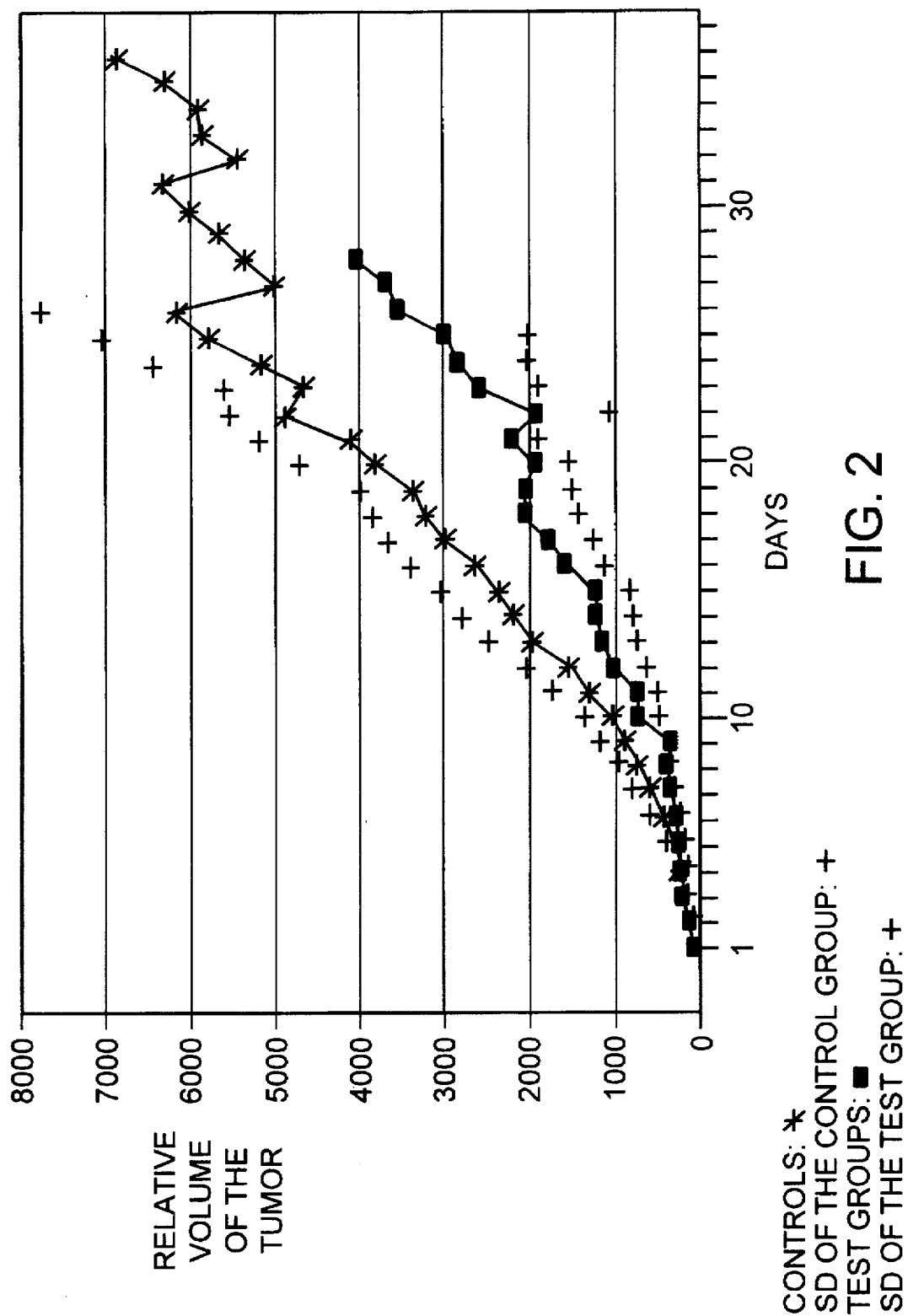
FIG. 2 shows the effect of a composition according to the present invention on melanoma B16 volume in C57B16 mice as compared to a control group.
Figure 3:
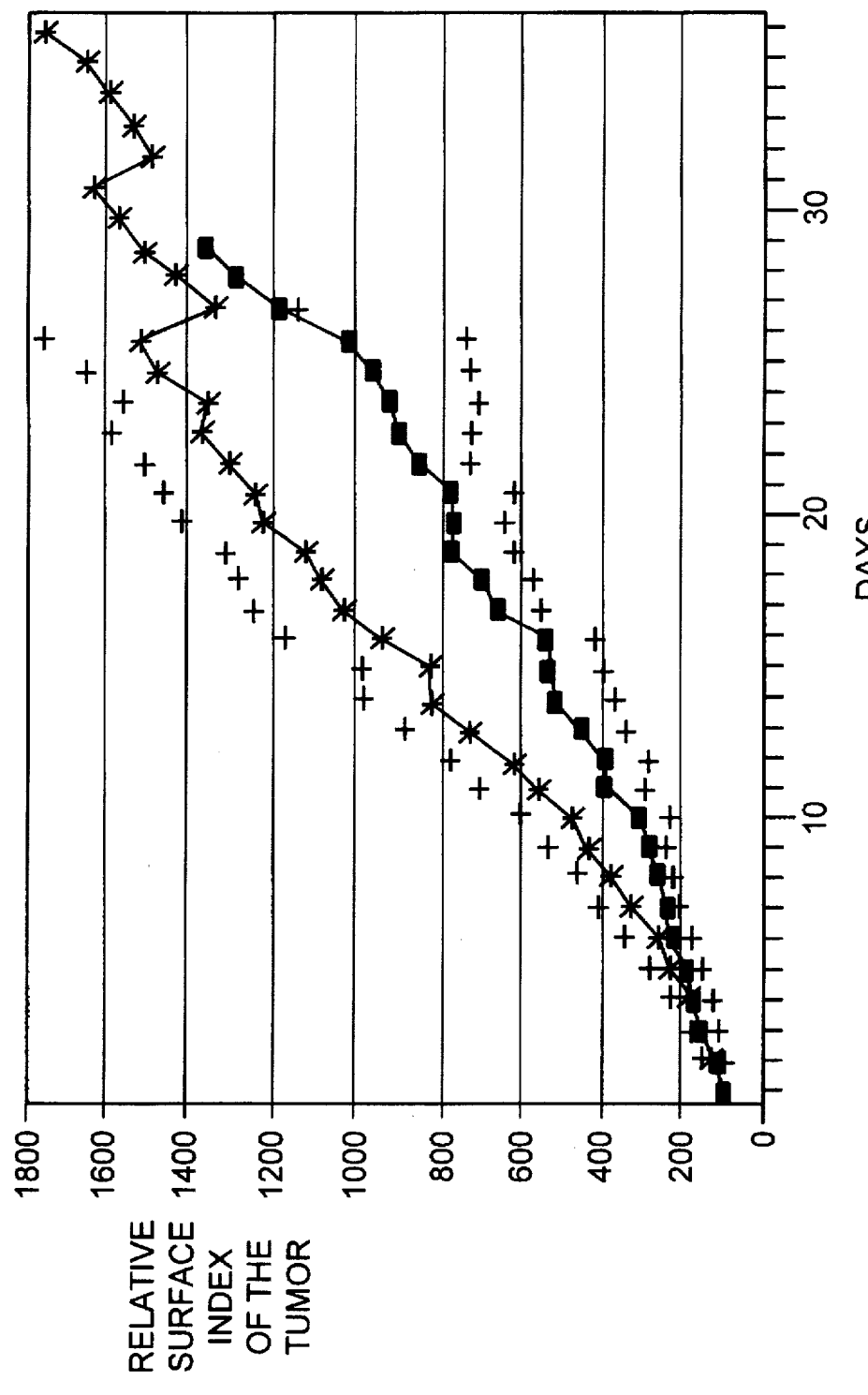
FIG. 3 shows the effect of a composition according to the present invention on the relative surface index of melanoma B16 in C57B16 mice as compared to a control group.

Composition of a Pharmaceutical Preparation According to Embodiment A:

10 g D-ribose 10 g 2-deoxy-D-ribose 2 g DL-alpha-alanine 2 g nicotinic 7 g ascorbic acid
dissolved in 1,000 g of physiological saline.

Example 2

Activity of the Preparation of Example 1 on the Production of Specific Antibodies Specific antibodies were determined by ELISA In the serum of C3H mice he seventh day after immunisation by ovalbumine. The preparation according to the embodiment A was given repeatedly, 5 times 0.2 ml i.p. The results are given in the following table:

| group | antibodies* | % of the control |
|---|---|---|
| controls | 672.8 ± 55.62 | 100 |
| test group | 1055.3 ± 387.6 | 156.8 |

*mean ± SD

From the values given in the Table it is clear that the pharmaceutical preparation according to this embodiment significantly promotes producing of specific antibodies.

Example 3

Activity of the Preparation According to the Embodiment A (Example 1) on the Proliferation of Splenocytes Induced by Mitogens and on Mixed Lymphocyte Reaction The test was performed by using the method of pending droplets. The preparation according to the embodiment A was given in an amount 3×0.2 ml i.p. to C3H-mice. One day following the last application the spleens were removed and the tests were performed. As mitogens Concavallin A (CON A), Phytohaemagglutinine (PHi), and lipopolysaccharides (LPS)were used. In the test on mixed lymphocyte cultures (MLR) splenocytes from DBA/1-mice were used as alloantigens The results of this tests are given in the following Table.

From the results it is quite clear that the preparation of the invention according to this embodiment does not stimulate the proliferation of lymphocytes induced by CON A, PHA and LPS, it is even possible to notice an inhibition of this proliferation.

| Group | dpm ± SE | % of controls |
|---|---|---|
| CON A | | |
| controls | 834.8 ± 175.0 | 100 |
| test group | 490.7 ± 70.9 | 58.8 |
| PHA | | |
| controls | 1065.4 ± 306,0 | 100 |
| test group | 593.7 ± 125.9 | 55.7 |
| LPS | | |
| controls | 1068.9 ± 274.4 | 100 |
| test group | 521.8 ± 96.7 | 44.8 |
| MLR | | |
| controls | 494.2 ± 49.6 | 100 |
| test group | 477.3 ± 97.2 | 96.6 |

Example 4

Quantitative Composition of the Pharmaceutical Preparation According to the Invention, Embodiment B 35 g D-ribose
35 g 2-deoxy-D-ribose
12 g DL-alpha-alanine
10 g nicotinic acid
20 L-ascorbic acid
dissolved in 1,000 ml of physiological saline.

Example 5

Activity of the Pharmaceutical Preparation According to Embodiment B on the Production of Specific Antibodies Specific antibodies were determined by ELISA in the serum of C3H mice the seventh day after immunisation with ovalbumine. The preparation according to the embodiment B was given repeatedly, 5 times 0.2 ml i.p. The results are given in the following table.

| Group | antibodies* | % of controls |
|---|---|---|
| controls | 672.8 ± 55.62 | 100 |
| test group | 592.4 ± 95.4 | 88 |

*mean ± SD

From the results it is clear that the pharmaceutical preparation according to embodiment B does not stimulate the production of specific antibodies.

Example 6

Activity of the Preparation According to the Embodiment B on the Proliferation of Splenocytes induced by Mitogens and on Mixed Lymphocyte Reaction The test was performed using the method of pending droplets. The preparation according to the embodiment B was applied in an amount of 3×0.2 ml i.p. to C3M-mice. One day after the last application the spleens were removed and the tests were performed. As mitogens Concavallin A (CON A), Phytohaemagglutinine (PHA), and lipopolysaccharides (IFS) were used. In the test on mixed lymphocyte cultures (MLR) splenocytes from DBA/1-mice were used as alloantigens.

| Group | dpm ± SE | % of controls |
|---|---|---|
| CON A | | |
| controls | 834.8 ± 175.00 | 100 |
| test group | 1109.4 ± 225.3 | 132.9 |
| PHA | | |
| controls | 11065.4 ± 306.0 | 100 |
| test group | 1475.6 ± 213.4 | 138.5 |
| LPS | | |
| controls | 1068.9 ± 274.4 | 100 |
| test group | 1500.6 ± 258.2 | 140.4 |
| NLR | | |
| controls | 494.2 ± 49.6 | 100 |
| test group | 411.0 ± 47.7 | 83.2 |

From the results it is clear that pharmaceutical preparation according to the embodiment B insignificantly stimulates the proliferation of lymphocytes induced by CON A, PHA and LPS.

Remark:

In the test no usual standards was used as the World Health Organization has not yet established a suitable and generally valid Immunomodulating preparation with which other or new preparations should be compared (the problem of the definition of the characters of an immunomodulating preparation has already been discussed in paragraphs concerning the known state of art).

Example 7

Activity of the Pharmaceutical Preparation According to the Embodiment B on the Growth of the Melanoma B16 in mice Mice melanoma B16 was implanted to 20 mice of the strain C57B16 intracutaneously at the right side. After inhealing of the transplantate the pharmaceutical preparation was applied after the conversion of the amount used to the body surface man/mouse according to Grossmann V., Jarkovska L., Kvetina J.: Farmacie 9, 1988:400–404. That means that each mouse obtained always 0.04 ml of the preparation according to the embodiment B into the tail vein. The preparation was applied during 28 days twenty times with an interval of two days after each fifth application. Control mice obtained the same amount of physiological saline (10 mice with transplantated melanoma B16). Each three days the tumors were observed and their size was estimated by the use of a slide calliper. A the same time the growth curve and the weight of the mice was estimated. During the course of the therapy by the use of the pharmaceutical preparation according to the embodiment B it was possible to prove a significant difference among the sizes of the tumours of the test groups and of controls. After the end of the therapy this difference was already not significant. It will apparently be necessary to find out the optimal schedule of application of the pharmaceutical preparation and to state the correlation among the activity of this preparation and the among of the tumour mass before the beginning of the therapy.

On the graphs 1, 2 and 3 the weight change of mice, relative volume and relative surface index of the tumour is given, respectively.

Example 8

Activity of the Pharmaceutical Preparation According to the Embodiment B on the Course of Leukemia in Rats In an orientation test the course of leukemia in rats of the strain SD/Ipcv was followed by estimating the weight, surviving of the rats and also haematological values. The haematological values for individual types of cells before the application of the preparation according to the embodiment B were as follows:

erythrocytes 8,050,000
leucocytes 12,300
thrombocytes 826,000
differentially:
blastic elements 4
myelocytes 0
metamyelocytes 6
rods 0
segments 25
eosinophiles 0
monocytes 4
lymphocytes 56
X-cells 9

The preparation was applied into the tail vein, the amount used was stated according to the ratio of body surface man/mouse (see Example 7).

After the fifth dose the haematological values changed in a following manner:

erythrocytes 7,350,000,
leucocytes 10,900
thrombocytes 982,000
differentially:
blastic elements: 4
myelocytes 0
metamyelocytes 3
rods 0
segments 46
eosinophiles 0
monocytes 3
lymphocytes 35
X-cells 9

Identical values were estimated every week. After the end of the therapy following values were obtained:

erythrocytes 6,310,000
leucocytes 9,300
thrombocytes 1,162,000
differentially:
blastic elements 0
myelocytes 0
metamyelocytes 0
rods 2
segments 39
eosinophiles 0
monocytes 6
lymphocytes 51

After the end of the therapy the animals were kept for 4 further weeks, at the end of that time following values were obtained:

erythrocytes 8,700,000
leucocytes 8,400
thrombocytes 778,000
differentially:
blastic elements 0
myelocytes 0
metamyelocytes 0
rods 1
segments 22
eosinophiles 1
monocytes 4
lymphocytes 72
X-cells 0

During the whole test the weight of the animal was estimated. This value did not change significantly in the course of 8 weeks and the clinical state of the animal also did not significantly change. From the results it is clear that under the therapy by the use of the pharmaceutical preparation according to the embodiment B it was possible to "normalize" the haematologic picture of the treated animals.

The results obtained in this example will serve as a starting material for targeted tests concerning the activity of the pharmaceutical preparation on haematoloical morous diseases and also on osteoporosis under conditions setted for pharmaceutical preparations for treatment of tumorous diseases.

Example

Limit Test for Acute Toxicity After a Single i.v. and i.p. Application of the Preparation According to the Embodiment B in Mice and Rats For performing the tests mice of the strain NMRI at the age of 6 weeks from a conventional breeding were used. The weight of males was 31 to 37 g, the weight of females was 27.5 to 32 g in the case of i.v. application, in the case of i.p. application the weight of males was 32 to 37 g and the weight of females was 28 to 33.5 g.

The preparation according to the embodiment B was applied in a volume of 2 ml/100 g in both modes of application. The i.v. application was performed into the tail vein, the i.p. application into the left lower quarter of the peritoneal cavity. The animals were kept in an air-conditioned room with a controlled regimen (12 hours light, 12 hours darkness, temperature of 23° to 25° C., relative humidity 50 to 70%) in polypropylene cages (Type T3 Velaz) in groups of 5 animals in the case of females. Males were kept individually because of their agressivity in polypropylene cages (Type T2 Velaz) on a litter of sterilized wood shavings. The animals obtained a pelleted diet ST 1 (Velaz) and drinking water ad libitum during the whole duration of the test.

The clinical state of health and the behaviour of the animals were followed every day during 21 days after the application of the preparation, the weight of the animals was estimated once a week. At the end of this time period all animals were subjected to macroscopical pathological investigation.

The tests were performed according to the internationally valuable OECD regulations for studies of acute toxicity.

Clinical investigations. After the i.v. application deepened regular breezing was observed (immediately after the application till 30 minutes after the application), then till the end of the time period fop which the animals were followed it was not possible to observe any clinical symptoms of toxicity. The growth curves also did not show any significant changes proving an optional toxic effect of the pharmaceutical preparation applied. After the i.p. application agin deepened breezing was observed, as weal as spastic walking together with traces of "write" spasms. After 30 minutes and through all following time period the animals did not develop any clinical symptoms of toxicity. During the abovementioned tests it was not possible to observe any dying of mice neither after i.v. application, nor after i.p. application. At the end of he time period of 21 days the animals were subjected to macroscopic pathological investigation. After i.v. application no pahological deviation against the normal state could be proved neither in males, nor in females in the organs of peritoneal and chest cavity and also in the place of the application no pathological changes could be observed. The observations in the case of the i.p. application were identical: on the surface of the spleen whitish coating could be observed, the spleen was partly or wholly attached to the stomach, the kidneys were a little lighter.

According to the abovementioned results the limit test for acute toxicity under internationally valuable regulations of the OECD concerning the studies of acute toxicity of a pharmaceutical preparation did not prove for a dose of 20 ml/kg after i.v. or i.p. application to mice of both sexes any symptoms of toxicity and it was also not possible to prove dying of the mice.

For further tests rats of the strain Wistar in the age of 6 weeks were used (conventional breeding). The weight of males was 194 to 209 g and of females 159 to 170 g in the case of the i.v. application, in the case of the i.p. application the weight of males was 190 to 215 g and of females 161 to 175 g.

The preparation according 2 to the embodiment B was applied in an amount of 2 ml/100 g in both types of application. The i.v. Duplication was performed into the tail vein, the i.p. application was performed into the left higher quarter of the peritoneal cavity. The animals were kept in an air-conditioned room with a controlled regimen (12 hours light, 12 hours darkness, temperature of 23° to 25° C., relative humidity 50 to 70%) in polypropylene cages (Type T4 Velaz) in groups of 5 animals of identical sex on a litter of sterilized wood shavings. The animals obtained a standard pelleted diet ST 1 (Velaz) and drinking water ad libitum during the whole duration of the test.

The clinical state of health and the behaviour of the animals were followed every day during 21 days after the application of the preparation, the weight of the animals was estimated once a week. At the end of this time period all animals were subjected to macroscopical pathological investigation.

The tests were performed according to the internationally valuable OECD regulations for studies concerning the acute toxicity.

Clinical investigations: after the i.p. and also after the i.v. application deepened regular breezing was observed together with slight limpness which could be observed till 5 hours after he application of the preparation. Throughout the remaining time period the animals did not show any clinical symptoms. The growth curves also did not show any significant changes proving an optional toxic effects of the pharmaceutical preparation applied. During the test no animal died after the i.v. or after the i.p. application of the rpeparation.

At the end of the period of 21 days for which the animals were followed the animals were subjected to macroscopical pathological investigation. After the i.v. application no pathological deviation against the normal state could be observed neither in males nor in females in the organs of peritoneal and chest cavity, also the place of the application remained without any pathological changes. Only the kidneys were a little lighter. After the i.p. application the observations for males and females were identical: on the surface of the spleen whitish coating could be observed, the spleen was partly or wholly attached to the stomach, the liver lobes were attached together and had whitish coatings, the kidneys were slightly lighter.

Histological investigation were performed over the scope of investigations required by the OECD regulations. On the liver it was possible to observe local chronical productive hepatitis, the liver parenchyma was without pathological changes. The finding on the liver were under normal limits, hyalinous deposits could be found in some epithelial cells of the liver cortex.

According to the abovementioned results the limit test for acute toxicity, performed under the OECD regulations for acute toxicity tests of a pharmaceutical composition according to the embodiment B in an amount of 20 ml/kg i.v. or i.p. din not cause in rats of both sexes any significant toxical symptoms. No animal died during the test.

What I claim is:

1. A pharmaceutical composition for immunomodulating and adjuvant treatment comprising:
    (a) a D-ribose in an amount ranging from about 32 to 63 wt %, (b) a deoxy-derivative of a D-monosaccharide in an amount ranging from about 32 to 63 wt % (c) DL-alpha-alanine in amount ranging from about 6 to 29 wt %, (d) nicotinic acid in an amount ranging from about 6 to 24 wt %, and (e) L-ascorbic acid ranging from about 22 to 45 wt % %, based on the total weight % of the composition.

2. The composition of claim 1, wherein the composition is dissolved in physiological saline.

3. The composition of claim 1, wherein the deoxy derivative of a D-monosaccharide is 2-deoxy-D-ribose.

4. The composition claim 1, wherein the composition further comprises (a) thiamine in an amount ranging from about 0.6 to 6 wt %, and (b) glutamic acid amide in an amount ranging from about to 0.03 to 48 wt %, based on the total weight % of the composition.

5. The composition of claim 1, wherein the D-ribose is present in an amount ranging from about 10 to 35 g, (b) the 2-deoxy-D-ribose is present in an amount ranging from about 10 to 35 g, (c) DL-alpha-alanine is present in an amount ranging from about 2 to 12 g, (d) nicotinic acid in an amount ranging from about 2 to 10 g, (e) L-ascorbic acid ranging from about 7 to 20 g, based on the total weight % of the composition.

6. The composition of claim 5, wherein the composition is dissolved in about 1000 g of a physiological saline.

7. The composition of claim 5, wherein the deoxy derivative of a D-monosaccharide is 2-deoxy-D-ribose.

8. The composition of claim 5, wherein the thiamine is present in an amount ranging from about 0.2 to 2 g and the glutamic acid amide is present in an amount of about ranging from about 0.01 to 15 g.

9. A method for stimulating the production of cytokines in a patient by intravenous application of a composition dissolved in physiological saline, said composition comprising:

(a) a D-ribose in an amount ranging from about 32 to 63 wt %, (b) a deoxy-derivative of a D-monosaccharide in an amount ranging from about 32 to 63 wt %

(c) DLalpha-alanine in amount ranging from about 6 to 29 wt %, (d) nicotinic acid in an amount ranging from about 6 to 24 wt %, and (e) L-ascorbic acid ranging from about 22 to 45 wt % %, based on the total weight % of the composition.

10. The method of claim 9, wherein the deoxy derivative of a D-monosaccharide is 2-deoxy-D-ribose.

11. The method of claim 9, wherein the D-ribose is present in the composition in an amount ranging from about 32 to 63 wt %, (b) the deoxy derivative of a D-monosaccharide is present in an amount ranging from about 32 to 63 wt % (c) the DL-alpha-alanine is present in an amount ranging from about 6 to 29 wt %, (d) the nicotinic acid is present in an amount ranging from about 6 to 24 wt %, and (e) the L-ascorbic acid is present in an amount ranging from about 22 to 45 wt %.

12. The method of claim 11, wherein the deoxy derivative of a D-monosaccharide is 2-deoxy-D-ribose.

13. The method of claim 11, wherein the composition further comprises (a) thiamine in an amount ranging from about 0.6 to 6 wt %, and (b) glutamic acid amide in an amount ranging from about to 0.03 to 48 wt %.

14. The method of claim 11, wherein the D-ribose is present in the composition is present in an amount ranging from about 10 to 35 g, (b) the 2-deoxy-D-ribose is present in an amount ranging from about 10 to 35 g, (c) DL-alpha-alanine is present in an amount ranging from about 2 to 12 g, (d) nicotinic acid in an amount ranging from about 2 to 10 g, (e) L-ascorbic acid ranging from about 7 to 20 g.

15. The method of claim 13, wherein the thiamine is present in an amount ranging from about 0.2 to 2 g, and the glutamic acid amide is present in an amount of about ranging from about 0.01 to 15 g.

16. A pharmaceutical composition for immunomodulating and adjuvant treatment made by combining:

(a) a D-ribose in an amount ranging from about 32 to 63 wt %, (b) a deoxy-derivative of a D-monosaccharide in an amount ranging from about 32 to 63 wt % (c) DL-alpha-alanine in amount ranging from about 6 to 29 wt %, (d) nicotinic acid in an amount ranging from about 6 to 24 wt %, and (e) L-ascorbic acid ranging from about 22 to 45 wt % %, based on the total weight % of the composition.

17. The composition of claim 16, wherein the composition is dissolved in physiological saline.

18. The composition of claim 16, wherein the deoxy derivative of a D-monosaccharide is 2-deoxy-D-ribose.

19. The composition claim 16, wherein the composition further comprises (a) thiamine in an amount ranging from about 0.6 to 6 wt %, and (b) glutamic acid amide in an amount ranging from about to 0.03 to 48 wt %, based on the total weight % of the composition.

20. The composition of claim 16, wherein the D-ribose is present in an amount ranging from about 10 to 35 g, (b) the 2-deoxy-D-ribose is present in an amount ranging from about 10 to 35 g, (c) DL-alpha-alanine is present in an amount ranging from about 2 to 12 g, (d) nicotinic acid in an amount ranging from about 2 to 10 g, (e) L-ascorbic acid ranging from about 7 to 20 g, based on the total weight % of the composition.

21. A method for stimulating the production of cytokines in a patient by intravenous application of a composition capable of being dissolved dissolved in physiological saline, said composition made by combining:

(a) a D-ribose in an amount ranging from about 32 to 63 wt %, (b) a deoxy-derivative of a D-monosaccharide in an amount ranging from about 32 to 63 wt %, (c) DL-alpha-alanine in amount ranging from about 6 to 29 wt %, (d) nicotinic acid in an amount ranging from about 6 to 24 wt %, and (e) L-ascorbic acid ranging from about 22 to 45 wt % %, based on the total weight % of the composition.

* * * * *

UNITED STATES PATENT AND TRADEMARK OFFICE
CERTIFICATE OF CORRECTION

PATENT NO. : 5,672,590
DATED : September 30, 1997
INVENTOR(S) : Kufudaki

It is certified that error appears in the above-identified patent and that said Letters Patent is hereby corrected as shown below:

On the Cover Page:

Section [86]: After "§ 371 Date", please delete "Apr. 10, 1996" and insert --Dec. 19, 1995--.

After "§ 102(e) Date", please delete "Apr. 10, 1996" and insert --Dec. 19, 1995--.

Signed and Sealed this

Sixth Day of January, 1998

*Attest:*

BRUCE LEHMAN

*Attesting Officer*    Commissioner of Patents and Trademarks